(12) United States Patent
Castelli et al.

(10) Patent No.: US 6,352,698 B1
(45) Date of Patent: *Mar. 5, 2002

(54) USE OF COMPLEXES FOR THE PREPARATION OF COMPOSITIONS FOR THE TREATMENT OF SENSITIVE SKIN, PREPARATION PROCESS AND HYPOALLERGENIC COMPOSITIONS

(75) Inventors: Dominique Castelli, Paris (FR); Gerd Ries, Düsseldorf (DE); Laurence Friteau, Créteil (FR); Elisabeth Bousigniere, Clichy (FR); Laurent Fredon, Courbevoie (FR)

(73) Assignee: Johnson & Johnson Consumer France, SAS, ROC Division, Issy les Moulineaux (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/293,111

(22) Filed: Apr. 16, 1999

(30) Foreign Application Priority Data

Oct. 22, 1996 (FR) .............................. 96 12821
Oct. 21, 1997 (WO) ................. PCT/IB97/01318

(51) Int. Cl.$^7$ ................................................. A61K 7/00
(52) U.S. Cl. .................... 424/401; 424/520; 424/195.1; 514/2; 514/23; 514/458; 514/844; 514/937
(58) Field of Search ................................ 424/401, 520, 424/195.1; 514/2, 23, 458, 844, 937

(56) References Cited

U.S. PATENT DOCUMENTS

| | | | | |
|---|---|---|---|---|
| 5,387,579 A | * | 2/1995 | Meybeck et al. | 514/100 |
| 5,443,839 A | * | 8/1995 | Meybeck | 424/450 |
| 5,643,598 A | * | 7/1997 | Meybeck | 424/450 |
| 5,656,618 A | * | 8/1997 | Meybeck et al. | 514/100 |

FOREIGN PATENT DOCUMENTS

WO    WO 98/17246    * 4/1998

* cited by examiner

Primary Examiner—José G. Dees
Assistant Examiner—Michael A. Williamson

(57) ABSTRACT

The present invention relates to the use of at least two compounds chosen from components having an a) anti-radical, b) anti-inflammatory and c) anti-allergic activity for the preparation of a composition exhibiting at least two of the a), b) and c) activities intended for the treatment of sensitive and/or allergic skin. It also relates to a process for the preparation of such compositions and to the compositions thus obtained.

9 Claims, 2 Drawing Sheets

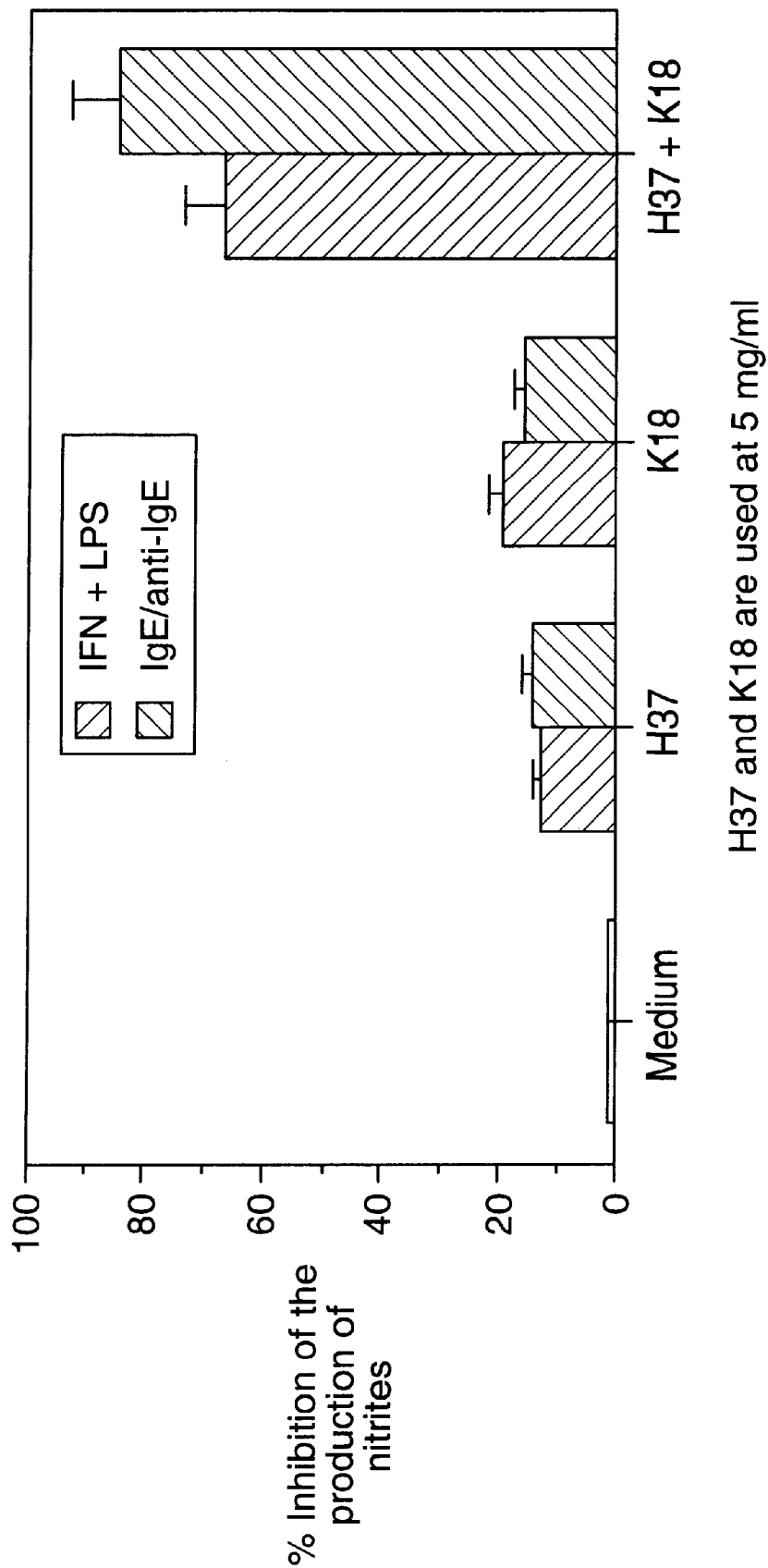

Figure 1:
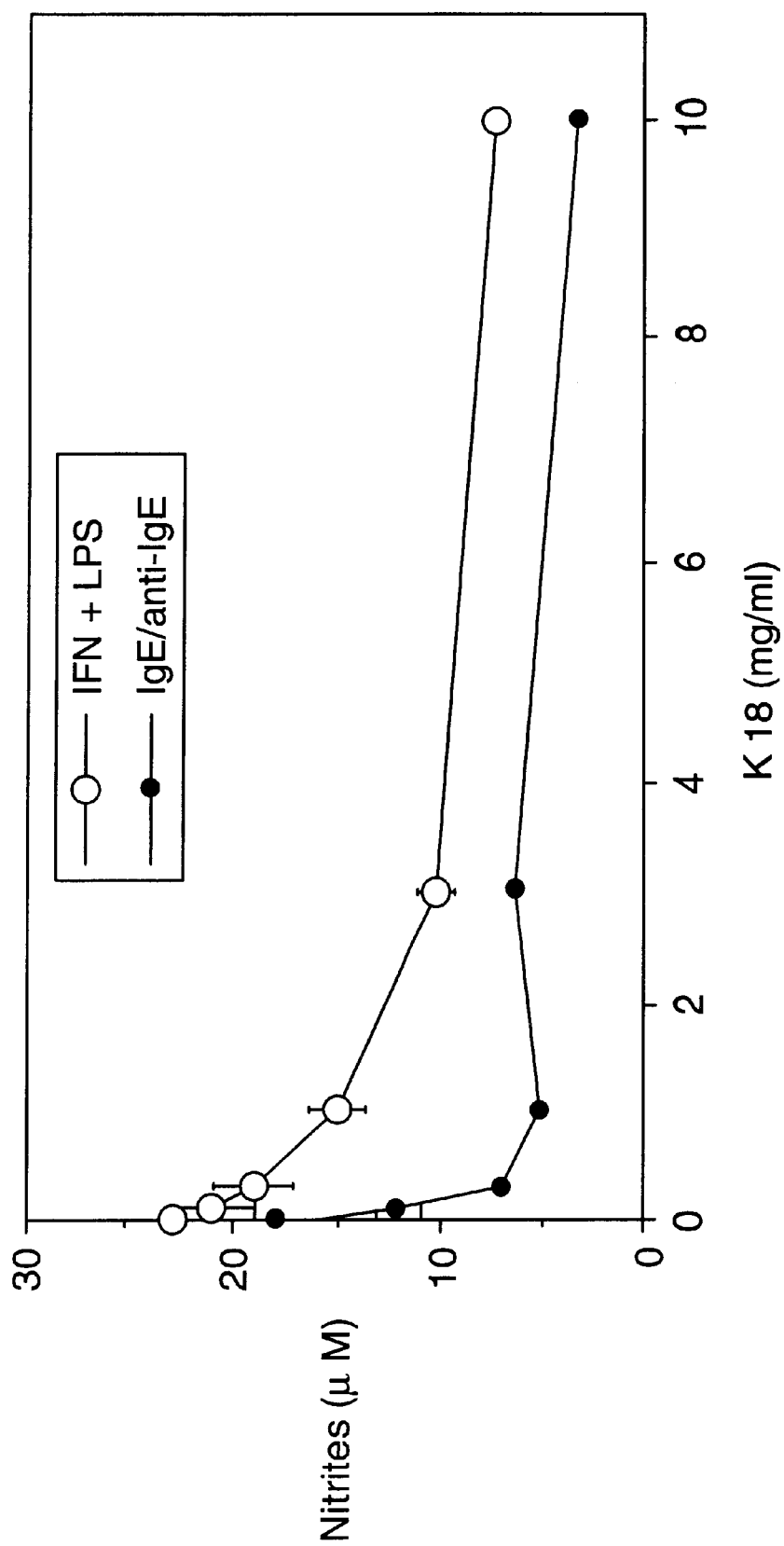

USE OF COMPLEXES FOR THE PREPARATION OF COMPOSITIONS FOR THE TREATMENT OF SENSITIVE SKIN, PREPARATION PROCESS AND HYPOALLERGENIC COMPOSITIONS

The invention relates to new dermocosmetic and pharmaceutical compositions which are useful for improving and treating hyperreactive skin conditions and more generally allergic-type reactions and/or intolerance phenomena, whether they are caused by external factors or factors intrinsic to the individual.

Increasing numbers of children and adults are in fact exhibiting skin described as "sensitive". During a recent study in France, 70% of the women questioned stated that they had sensitive facial skin. The notion of sensitive skin covers an array of outward signs comprising reactive skin and intolerant skin. Atopic skin can also be included therein. These skin types are sometimes incorrectly known as "allergic " by the subjects; however, while an allergic component can sometimes be evoked in the symptoms of sensitive skin, it may not be restricted to it. The triggering factors can be environmental attacks such as wind, pollution, temperature variations, excessively hard water or ill-suited hygiene, cosmetic or care products; these phenomena can also be associated with stress or emotions felt by the subject, some diets or the taking of medicaments. In addition, there exists individual predisposing factors (in particular neurological or hormonal) or familial predisposing factors which amplify these reactions.

Generally, the subject feels cutaneous discomfort which can manifest itself by subjective and/or objective signs. The skin readily gives off stabbing pains, itches or smarts and the subject may experience feelings of warmth, pricking or burning on the skin. The skin can redden or desquamate. Xerosis, seborrhoeic dermatitis, telangiectasias, vesicles or even oedema is observed, on an irregular basis.

In the most serious cases, dermatological complaints of immunoallergic type, such as atopy, eczema or neurodermatitides, may be observed.

This condition can manifest itself on the skin, the mucous membranes or the scalp. In the latter case, it may be associated with a dandruff condition and/or alopecia.

Until now, attempts have been made to prevent the appearance of these reactions by limiting the presence, in dermocosmetological formulations, of components known to be allergizing. However, it would be desirable to be able to have available truly active compositions which are capable of preventing or of relieving these symptoms by decreasing the reactivity of the skin and by improving its resistance to the triggering factors.

The Applicant Company has now found, unexpectedly, that these aims could be achieved by the use of a composition containing a synergic combination producing an active hypoallergenic complex.

Such a complex will, in addition, improve the receptivity of the skin towards other active principles.

For this reason, the subject of the present invention is a dermocosmetic composition, characterized in that it contains an immunomodulatory or hypoallergenic synergic combination of at least two components, each of these components exhibiting at least one of the following activities:

a) anti-radical
b) anti-inflammatory
c) anti-allergic, the said components being chosen so that at least two activities a), b) or c) are present in the composition.

The subject of the invention is more particularly the use of at least two compounds chosen from components having an a) anti-radical, b) anti-inflammatory and c) anti-allergic activity for the preparation of a composition, in particular an immunomodulatory composition, exhibiting at least two of the a), b) and c) activities intended for the treatment of sensitive and/or allergic skin; according to one of its aspects, the a), b) and c) activities are exerted in the composition.

Indeed, the Applicant Company has been able to show that the combination of active principles having complementary anti-allergic, anti-radical and/or anti-inflammatory activities made it possible to effectively combat the phenomena associated with the appearance of the symptoms of sensitive and/or intolerant skin or of immunoallergic complaints, preferably via a synergy of the activities of the components.

The components forming part of the formulations according to the invention can be purified or unpurified molecules, synthetic or extracted products, mixtures of active principles or extracts which have been subjected to one or a number of fractionation stages from a starting material of plant or animal origin.

Preferably, if two components present in the formulation show an activity of the same type, it will be exerted by the involvement of a different mechanism.

As regards the anti-inflammatory activity, it can in particular be provided by prostaglandin inhibitors (cyclooxygenase route), inhibitors of cytokine production and inhibitors of the production of leukotrienes (LTB, for example, lipoxygenase route).

The component or components with anti-inflammatory activity advantageously exhibit an inhibiting activity on the production of IL-1, IL-2, IL-4, IL-5, IL-12 and/or TNF-$\alpha$ (Tumour Necrosis Factor).

The anti-inflammatory function can also have the consequence of decreasing the production of reactive nitro derivatives by the cells, limiting the generation of free radicals.

However, anti-radical activity is understood to mean components which are preferably chosen from free-radical scavengers, anti-lipoperoxidants and stimulants of the endogenous production of the enzymes which degrade free radicals.

Free radicals, by definition, are neutral or charged chemical species which have an unpaired electron. This "single electron" endows them with specific chemical properties and a short lifetime. They are reaction intermediates which will be stabilized by combination or transfer and can be the source of a chain reaction. Mention may be made, among free radicals, of the superoxide anion $O_2$ the hydroxyl radical OH , NO or peroxides.

Enzymes which are active in endogenous defense systems against free radicals are, for example, SOD (or superoxide dismutase), catalase or glutathione peroxidase; attempts will be made to stimulate the production of these enzymes or they can be introduced exogenously.

The components providing the anti-allergic function in the composition according to the invention are preferably chosen from inhibitors of lymphocyte proliferation, inhibitors of the internalization of the molecules of the major histocompatibility complex (HLA-DR, for example) or inhibitors of cytokine production. They are advantageously capable of decreasing the production of the mediators of the inflammation which occurs during allergic phenomena.

As indicated above, the composition will exhibit at least two of the anti-radical, anti-inflammatory and anti-allergic activities. In addition, the components of the active hypoallergenic complex will be chosen so that a synergy is exerted via different mechanisms at the basis of the same activity.

Each component will preferably contribute, via a number of parameters, to the overall activity of the composition according to the invention.

The composition according to the invention advantageously has a marked inhibiting activity on the synthesis and/or the expression of neuromediators, in particular with respect to cutaneous cells, resulting from a synergy of the activities of its different components. The neuromediators can be chosen from the group comprising neurokinines A (NKA) and B (NKB), vasoactive intestinal polypeptide (VIP), calcitonin gene related peptide (CGRP), neuropeptide Y (NPY), neurotensin (NT), somatostatin (SOM), gastrin releasing peptide (GRP), nerve growth factor (NGF), PGP 9.5 (Protein Gene Product 9.5) and bombesin.

Components making possible the preparation of dermocosmetic compositions according to the invention can advantageously be chosen from the following group: Ginkgo biloba and its extracts, iramine, D-panthenol, β-sitosterol, modulene, α-tocopherol and its derivatives, β-glucan and its derivatives, eicosapentanoic acid, 18β-glycyrrhetinic acid, glycyrrhetinic acid monoglucuronide, stearyl glycyrrhetinate, Scutellaria extract, lactoferrin, green tea and its extracts, vitamin C, glutathione, epidermal thymus factor, azole derivatives and lipacid.

However, the combination of vitamin E with a Scutellaria extract is not included within the compositions according to the invention.

According to one of the aspects of the invention, the composition contains at least one component, preferably at least two components, chosen from the above group.

The azole derivatives used according to the invention can be chosen from imidazole or triazole derivatives and in particular from the group composed of: bifonazole, butoconazole, chlordantoin, chlormidazoie, cloconazole, clotrimazole, econazole, enilconazole, fenticonazole, flutrimazole, isoconazole, ketoconazole, lanoconazole, miconazole, omoconazole, oxiconazole, sertaconazole, sulconazole, tioconazole, fluconazole, itraconazole, saperconazole, terconazole or elubiol.

This is because it has now been possible to demonstrate that these compounds exhibit in particular an anti-radical activity.

Mention may more particularly be made, among α-tocopherol derivatives which can be used, of α-tocopherol phosphate.

Mention may be made, among β-glucan derivatives, of carboxymethyl-β-glucan and drieline.

Drieline is a poly-β(1→3)-glucopyranose of formula

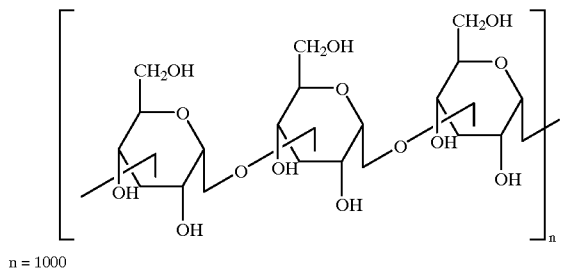

n = 1000 with n=1000.

The molecule can be provided in the form of a 0.1% solution in water and sorbitol or in the powder form.

In one of the preferred embodiments of the invention, the composition contains a synergic combination of a Ginkgo biloba extract and of a β-glucan compound.

Indeed, the Applicant Company has found that the combination of these two components made it possible to obtain the optimum combination of the functional characteristics providing the activity of the compositions according to the invention.

The glucan is composed of a β(1→3) glucose chain which can in particular be extracted from the wall of yeast cells. It is possible to subject it to chemical modifications in order in particular to improve its solubility.

The β-glucan is advantageously substituted by carboxymethyl groups; it can exist in the salt form, in particular the sodium salt form. Good results are obtained with a derivative in wich the degree of substitution by carboxymethyl groups is within the range from 0.65 to 0.85 and which exhibits a pH from 5.5 to 8.5.

Ginkgo biloba is a dioecious tree from the Far East, the leaves of which are used for certain medicinal properties. They contain constituents, such as aliphatic hydrocarbons and alcohols, polyphenols, such as luteolin or quercetol, or biflavones derived from amentaflavone, and more specific constituents: ginkgolic acid, and anacardic derivatives, terpenes derived from limonene or terpenes containing a tert-butyl group.

Ginkgo extracts have been proposed for improving the symptoms of mental deficiency in the elderly, of intermittent claudicatior, of obliterating chronic arteriopathies and of Raynaud's disease, or in the case of retinal deficiency.

They have been used in cosmetology for their protective effect with respect to free radicals.

The Applicant Company has found, unexpectedly, that ginkgo extracts have an excellent anti-inflammatory and anti-allergic activity which can be demonstrated on cutaneous cells, such as keratinocytes and macrophages. In addition, the Applicant Company has shown that this activity is potentiated in the presence of β-glucan.

Extracts which are particularly suitable for the implementation of the invention are obtained from Ginkgo biloba leaves which have been subjected to a stage during which the terpene concentration has been brought to a value of less than approximately 7% and preferably of less than approximately 3% (w/w of dry extract). In one of the embodiments, this terpene concentration is less than approximately 1% w/w.

The concentration of flavone heterosides in the dry extract is advantageously greater than 24% and preferably greater than approximately 28% w/w.

The anti-inflammatory and anti-allergic properties can be demonstrated in particular with respect to in vitro models, for which a correlation exists with animal models and clinical studies already carried out on man.

It is possible in particular to operate on keratinocytes and macrophage cells because these are cells which are essential for the development of a local inflammatory reaction. Moreover, macrophages are particularly advantageous cells because, due to the fact that these are resident cells in the skin, they regulate not only local inflammatory reactions but they also regulate the immune responses by their ability to present the antigen and to produce a great number of cytokines which regulate local immunity. These macrophages are also involved in communications with the circulatory system which can, if appropriate, mobilize different cell types (monocytes, neutrophils, eosinophils and T lymphocytes), thus increasing the non-specific and specific defensive power of the tissue under consideration.

The activities of the test products are therefore investigated with respect to human macrophage and keratinocyte cultures which are or are not stimulated by interferon-γ+ lipopolysaccharide (non-specific inflammation) or by IL-4 (allergic inflammation). This type of stimulation places the cells in the context of a pro-oxidizing response (generation of NO or superoxide anion free radicals, which can be evaluated by measuring the production of nitrogenous derivatives) and an immuno-inflammatory response (production of cytokines such as TNF-α).

To evaluate the allergic inflammation, the cells are activated by IL-4, which induces the CD23 receptor, and then by IgE-containing immune complexes. In all cases, the cellular supernatants are analysed after the activation.

A viability study is in addition carried out on the cells.

The activity of the components is also confirmed on mixed lympho-epidermal cultures (MLEC).

In the skin, Langherans cells indeed play an essential role in the presence of the antigen and keratinocytes generate factors which are involved in the immune response, thus constituting a cutaneous immune system. MLECs make it possible to determine the immuno-modulatory properties of substances by measuring the lymphocyte proliferation induced by the antigen-presenting allogenic epidermal cells, with or without treatment by the substance.

The results obtained with ginko and β-glucan are summarized in the table below:

| Activity | Mediator or parameter | Ginkgo biloba | β-Glucan |
|---|---|---|---|
| Anti-inflammatory | $LTB_4$ | inhibition | no effect |
| | $PGE_2$ | no effect | inhibition |
| | IL-1α | no effect | inhibition |
| | TNF-α | no effect | inhibition |
| Anti-free radicals | peroxidation of the lipids | inhibition | no effect |
| | NO | inhibition | inhibition |
| | catalase | no effect | stimulation |
| | glutathione peroxidase | stimulation | stimulation |
| Anti-allergic | MLEC | inhibition | no effect |

Compositions according to the invention contain in particular from 0.001% to 10% w/w of a ginko extract and preferably from 0.05 to 2%; according to one of the embodiments, the concentration of ginkgo extract will be from approximately 0.1 to 0.5% but it will be adjusted by the person skilled in the art.

Concentrations of β-glucan, in particular carboxymethylated β-glucan, which are suitable for the implementation of the invention are within the range from 0.001% to 10% w/total w of the composition.

Other compositions which are particularly suitable for the invention comprise the combination of lactoferrin and drieline, panthenol and green tea extract or panthenol and β-sitosterol. A combination of β-tocopherol (or one of its salts) and a ginkgo extract can also be used according to the invention. Such combinations produce an active hypoallergenic complex which lowers the reactivity threshold of the skin and of the scalp and decreases the magnitude of the possible intolerance or immunoallergic reactions.

The green tea extract is obtained from dry Camellia oleifera leaves and contains, in particular, theophylline, caffeine and theobromine.

Another subject of the invention is a process for the preparation of an active hypoallergenic complex, characterized in that substances belonging to at least one of the groups: anti-free radical, anti-inflammatory and immuno-modulatory active principle are selected and in that two substances having complementary activities are then combined so as to potentiate the anti-radical, anti-inflammatory and anti-allergic functions of the combination.

The combination of the substances constituting the active hypoallergenic complex preferably decreases the synthesis or the expression of the neuromediators, such as VIP, PGP 9.5 or CGRP, which are correlated with so-called "sensitive" or irritable skin.

Another subject of the invention is a method for the cosmetic treatment of sensitive skin comprising the application to the skin of the body or of the face, one or a number of times per day, of active hypoallergenic complexes and/or compositions as defined above.

In particular, the invention relates to a method for the treatment of alopecia which comprises the weekly, twice-weekly, daily or twice-daily application to the scalp of a combination of anti-radical, anti-inflammatory and/or anti-allergic components. The combinations can be in different formulations, such as shampoos or lotions, which can be applied simultaneously, separately or sequentially, optionally with other active principles which are active with respect to alopecia, dandruff conditions and/or seborrhoeic conditions.

Another of the subjects of the invention is the use of a hypoallergenic complex as defined above for the preparation of an immunomodulatory medicament, in particular intended for the treatment of a complaint chosen from atopy, psoriasis, erythema multiforme, xeroder-maztitides, lupus erythematosus, pemphigus, dermatitides, rosacea, acne, eczemas and neurodermatitides.

The hypoallergenic combinations according to the invention will advantageously be formulated within compositions also containing moisturizing agents and/or agents which improve cutaneous penetration, which will promote the activity of the complex according to the invention. Mention may be made, by way of examples, of urea, propylene glycol or oleic acid, the person skilled in the art being capable of using other penetration promoters suited to the type of formulation.

The compositions according to the invention will in addition contain pharmaceutically and/or cosmetologically acceptable excipients known to the person skilled in the art suited to their formulation, in particular in the form of solutions, lotions, creams, shampoos, emulsions, and the like.

Mention may be made, in a non-limiting way, of pigments, dyes, preservatives, texturing agents, thickeners, emulsifiers or fragrances. They can also contain sunscreening agents or blockers or another active principle.

Finally, the hypoallergenic complexes containing the combinations according to the invention can be introduced into compositions containing at least one active principle by the topical route, in particular when this active principle is capable of causing a cutaneous reaction.

Mention may more particularly be made, among such active principles, of retinoids and depigmenting active agents.

Retinoids is understood to mean in particular retinoic acid or tretinoin, retinol, retinaldehydes, their salts and their esters. The alkali metal, ammonium and $C_2$–$C_{30}$ ammonium salts are typical salts. The sodium, potassium, triethanolammonium and ammonium salts are particularly preferred. The combinations of all the above compounds can be present in the compositions. In addition, the terms "retinol" and "retinoic acid" must be understood as including the hydrogenated and non-hydrogenated isomers, such as 9-cis-retinol, didehydro-retinol, 13-cis-retinoic acid, 13-trans-retinoic acid and didehydroretinoic acid.

The depigmenting agents comprise, for example, kojic acid, hydroquinone, vitamin C, vitamin C magnesium phosphate, carotenoids, arbutin, and the like.

The following examples are intended to illustrate the invention.

In these examples, reference will be made to the following figures:

FIG. 1: Dose effect of carboxymethyl-β-glucan with respect to the inflammatory functions of the keratinocytes.

FIG. 2: Synergy between a Ginkgo biloba extract (H37) and carboxymethyl-β-glucan (K18) in their anti-inflammatory functions with respect to keratin-ocytes.

EXAMPLE 1

1. Materials and Methods

Products

The following products were used during this study: *Escherichia coli* LPS (Sigma), used at 1 µg/ml. IFN-γ and IL-4 are sourced from Immugenex (Los Angeles Calif.) and are used respectively at 1000 U/ml and 10 ng/ml, the monoclonal IgEs are sourced from Stallergène (Fresnes, France) and the anti-IgEs are from Nordic (Tilburg, Holland).

Keratinocyte culture

The keratinocyte primary cultures are obtained from neonatal foreskins and are maintained in proliferation ex vivo in a medium which does not contain calf serum. The confluent keratinocyte cultures are trypsinized and transferred into 24-well plates in fresh medium at the cellular density of $10^5$ cells/ml/well. If appropriate, in the case of stimulation by IL-4, the presence of the IgE receptor (CD23) at the surface of the cells is verified by immunolabelling.

Macrophage culture

The macrophage cells are obtained from the peripheral blood of normal donors (non-allergic). The mononuclear cells are isolated on a ficoll gradient and the ring of lymphoid cells is recovered and washed three times and the cells are then cultured so as to cause the macrophage cells to adhere. These cells are recovered after adhering for 1 hour and are cultured ($10^6$ cells/ml/well). If appropriate, in the case of stimulation by IL-4, the presence of the IgE receptor (CD23) at the surface of the cells is verified by immunolabelling.

Cell activation

The cells are activated by the combination of IFN-γ and LPS for 3 to 4 days and the supernatants of these cultures are then recovered in order to quantitatively determine the nitrogenous derivatives and TNF-α. Likewise, during stimulation by IgE, the cells are first activated by IL-4, so as to induce the CD23, and are then subsequently cultured and stimulated by the IgE-containing immune complexes for 3 to 5 days before recovering the different supernatants. In all the cases, cellular viability is achieved on conclusion of these cultures. In the specific case of macrophages, a long-term (7 to 12 days) viability study was carried out, so as to determine the protective effects of these products. Quantitative determination of the nitrogenous derivatives is carried out using the Gries approach and the TNF level is measured by using quantitative determination kits from Medgénix (Fleurus, Belgium).

2. Results

2.1. Effect of a Ginkgo biloba extract on the keratino-cytes and the macrophages stimulated by IFN-γ+ LPS

Dry Ginkgo biloba leaves were subjected to continuous extraction by an acetone/water mixture under vacuum and then several stages of removal of solvent as well as of chlorophyll, lipids, waxes, lectins and of certain substances result in an extract subsequently denoted by H37.

It exists in the form of a fine powder corresponding to the following specifications:

| residual solvents | |
|---|---|
| ethanol | <3% |
| acetone | <0.1% |
| butanol | <0.1% |
| ethyl acetate | <0.1% |
| sulphated ash | <1.5% |
| water content | <3% |
| pro-anthocyanidins | <5% |
| terpenes | <0.5% |
| ginkgolic acid | <10 ppm |
| heavy metals | <20 ppm |
| flavone heterosides | 32 ± 3% |

It is 6% (w/w) soluble in PEG 400 and 4% (w/v) soluble in 90° ethanol.

In this study, the product H37 (10 mg/ml) is added 30 min before stimulation by IFN-γ+ LPS. This product showed no cytotoxic activity.

TABLE 1A

Production of nitro derivatives ($NO_2^-$ µM) after stimulation by IFN-γ + LPS +/− 10 mg/ml H37

| Cells | | Expt-1 | Expt-2 | Expt-3 | Expt-4 |
|---|---|---|---|---|---|
| Macrophages | | 11(5)* | 15(5) | 5(3) | 2(9) |
| | +H37 | 7(4) | 8(4) | 2(2) | 2(2) |
| Keratinocytes | | 12(15) | 17(3) | 23(12) | 13(5) |
| | + H37 | 7(6) | 7(3) | 8(11) | 6(4) |

*The values between brackets are those of cells which have not been stimulated by IFN-γ + LPS

TABLE 1B

Production of TNF (pg/ml) after stimulation by IFN-γ + LPS +/− 10 mg/ml H37,

| Cells | | Expt-1 | Expt-2 | Expt-3 | Expt-4 |
|---|---|---|---|---|---|
| Macrophages | | 755(ND)* | 1250(155) | 998(55) | 1510(ND) |
| | +H37 | 605(ND) | 1120(75) | 895(50) | 1315(ND) |
| Keratinocytes | | 187(ND) | 173(ND) | 208(ND) | 135(ND) |
| | + H37 | 168(ND) | 165(ND) | 112(ND) | 105(ND) |

*The values between brackets are those of cells which have not been stimulated by IFN-γ + LPS, ND = non-detectable.

Through these experiments, it appears that the macrophages stimulated by IFN-γ+ LPS do not produce nitro derivatives to a significant extent whereas the keratinocytes produce it reproducibly. In fact, it has recently been demonstrated that, during such a stimulation, the macrophages produce a truncated NO synthase which could have a significant decrease in its activity, which is apparently not the case for the keratinocytes.

In the keratinocytes, H37 inhibits the production of NO after stimulation.

The product H37 exhibits a slight "anti-inflammatory" activity. Moreover, on evaluating the dose effect of H37 on this production by the keratinocytes, it is shown that the maximum effect is observed at 10 mg/ml.

In addition, H37 protects the macrophage cells from the cell death induced by radical products. The fact that the stimulated macrophages do not produce significant amounts of nitro derivatives does not rule out the fact that these cells are not subjected to an oxidative shock which can result in cell death.

This is objectivized by comparisons of the effects on the long-term cell viability at 10 days or with the short-term cultures (2 days). It appears that H37, at 10 mg/ml, protects the macrophage cells from the cell death induced most of the time by the radical products.

TABLE 2

Effect of H37 on the viability of the macrophages

| Macrophages + IFN/LPS | % of viable cells at D2 | % of viable cells at D10 |
|---|---|---|
| Medium | 85 ± 2 | 55 ± 7 |
| + H37 | 88 ± 3 | 80 ± 2 |

2.2. Effect of the product H37 on the macrophages and the keratinocytes stimulated by IL-4.

The cells are stimulated for 48 h in the presence of IL-4 (10 ng/ml), so as to induce the receptor with a low affinity for the IgEs (CD23) at their surface. On completion of this culturing period, 30 to 80% of the keratinocytes and of the macrophages express CD23. The individual variations are in no case the reflection of a different allergic situation between these individuals. Whatever the situation, in this induction phase, the tested product does not modify this induction of CD23; in fact, a decrease of less than 5% cannot be observed (n=8).

TABLE 3

Induction of the expression of CD23 by the different cells stimulated by IL-4 in the presence or in the absence of 10 mg/ml H37

| Cells | Medium | + IL-4 |
|---|---|---|
| Macrophages | <5% | 45 +/− 4 |
| +H37 | <5% | 41 +/− 2 |
| Keratinocytes | ND | 55 +/− 7 |
| +H37 | ND | 51 +/− 4 |

*The cells are stimulated for 48 h in the presence or in the absence of 10 ng/ml of IL-4 and in the presence or in the absence of the different products, ND = non-detectable.

After the CD23 has been taken up by IgE-containing immune complexes, the production of a large number of mediators and cytokines (in particular TNF) and of products resulting from the oxidative metabolism, such as nitrogenous derivatives, is induced. This stimulation redefines in vitro an allergic-type inflammatory reaction.

In-this case, the results observed are in every respect comparable with those obtained with IFN-γ and LPS, which tends to demonstrate that H37 exhibits certain anti-inflammatory activities (non-specific and allergic), probably via its ability to regulate the oxidizing abilities of the "inflamed" cells. The results obtained are summarized in the following two tables:

TABLE 4A

Production of nitro derivatives ($NO_2^-$ µM) after stimulation by IL-4 +/− 10 mg/ml H37

| Cells | | Expt-1 | Expt-2 | Expt-3 | Expt-4 |
|---|---|---|---|---|---|
| Macrophages | | 25(5)* | 30(2) | 55(11) | 15(2) |
| | +H37 | 15(2) | 17(75) | 21(50) | 6(2) |
| Keratinocytes | | 17(13) | 13(3) | 23(12) | 13(5) |
| | + H37 | 12(11) | 8(2) | 10(10) | 8(6) |

*The values between brackets are those of cells which have not been stimulated by the IgE-containing immune complexes.

The product H37 exhibits a good ability to inhibit the production of nitro derivatives by the macrophages and the keratinocytes stimulated by IL-4.

TABLE 4B

Production of TNF (pg/ml) after stimulation by IL-4 +/− 10 mg/ml H37

| Cells | | Expt-1 | Expt-2 | Expt-3 | Expt-4 |
|---|---|---|---|---|---|
| Macrophages | | 975 (105) * | 275 (35) | 455 (40) | 310 (89) |
| | +H37 | 850 (105) | 215 (25) | 365 (25) | 275 (87) |
| Keratinocytes | | 185 (ND) | 158 (ND) | 315 (35) | 308 (ND) |
| | + H37 | 155 (ND) | 120 (ND) | 245 (30) | 276 (ND) |

* The values between brackets are those of cells which have not been stimulated by the IgE-containing immune complexes, ND = non-detectable.

The product H37 induces a slight decrease in the production of TFN-α by the macrophages and the keratinocytes stimulated by IL-4.

Just as during the non-specific stimulation, it appears that H37 increases the long-term viability of the macrophages and of the keratinocytes stimulated by the IgE-containing immune complexes, which, again, suggests very strongly that the product H37 exerts its slight anti-inflammatory activity via an anti-oxidizing activity with respect to the target cells.

It therefore appears that the product H37 exhibits an anti-inflammatory activity (allergic or non-allergic). This characteristic is very important because the seriousness of the inflammatory responses, whether or not of allergic origin, results from an imbalance in the oxidative metabolism of these cells. It is in particular this imbalance which is the source, at least in part, of the regulation of the immunological phenomena associated with these reactions: this is the case for specific allergen reactions and for the production of cytokines.

2.3. Effect of the products K17 and K18 on the keratinocytes and the macrophages stimulated by IFN-γ+ LPS Drieline is denoted by K17. Drieline is a poly-β(1→3)-glucopyranose purified from *Saccharomyces cerevisiae* yeast membranes; it is in solution in a water/sorbitol mixture.

Carboxymethyl-β-glucan (sold under the trade name CM Glucan® by the company Arnaud) is denoted by K18.

In this study, the products (10 mg/ml or 1/100 v/v) are added 30 min before stimulation by IFN-γ+ LPS. In none of the cases have these products shown a cytotoxic activity.

TABLE 5A

Production of nitro derivatives ($NO_2^-$ in µM) after stimulation by IFN-γ + LPS +/− 10 mg/ml of the products K17 and K18

| Cells | | Expt-1 | Expt-2 | Expt-3 | Expt-4 |
|---|---|---|---|---|---|
| Macrophages | | 13(2)* | 8(5) | 9(6) | 3(2) |
| | +K17 | 5(2) | 2(1) | 7(1.5) | 2(2) |
| | +K18 | 6(1) | 4(1) | 5(1) | 1(2) |
| Keratinocytes | | 25(2)* | 28(5) | 19(6) | 13(2) |
| | +K17 | 15(2) | 16(1) | 15(1) | 8(2) |
| | +K18 | 13(1) | 14(1) | 11(1) | 7(1) |

*The values between brackets are those of cells which have not been stimulated by IFN-γ + LPS.

The products K17 and K18 have a high ability to inhibit the production of nitro derivatives by the macrophages and the keratinocytes stimulated by IFN-γ and LPS.

TABLE 5B

Production of TNF (pg/ml) after stimulation by IFN-γ + LPS +/− or 10 mg/ml of the products K17 and K18

| Cells | | Expt-1 | Expt-2 | Expt-3 | Expt-4 |
|---|---|---|---|---|---|
| Macrophages | | 612(ND)* | 920(155) | 903(55) | 700(ND) |
| | +K17 | 605(ND) | 902(95) | 970(45) | 695(ND) |
| | +K18 | 121(ND) | 320(125) | 512(20) | 333(ND) |
| Keratinocytes | | 205(ND) | 138(ND) | 145(ND) | 108(ND) |
| | +K17 | 125(ND) | 98(95) | 100(ND) | 70(ND) |
| | +K18 | 130(ND) | 95(ND) | 85(ND) | 82(ND) |

*The values between brackets are those of cells which have not been stimulated by IFN-γ + LPS, ND = non-dectectable.

The production of TNF-α by the macrophages and the keratinocytes stimulated by IFN-γ+ LPS is also detrimentally affected in the presence of the different products in a way comparable with that observed for the nitro derivatives. The products K17 and K18 efficiently inhibit the production of TNF.

2.4. Effect of the products K17 and K18 on the macrophages and the keratinocytes stimulated by IL-4.

The cells are stimulated for 48 h in the presence of IL-4 (10 mg/ml), so as to induce the receptor with a low affinity for the IgEs (CD23) at their surface. On completion of this culturing period, 30 to 80% of the keratinocytes and of the macrophages express CD23. The individual variations are in no case the reflection of a different allergic situation between these individuals. Whatever the situation, in this induction phase, none of the tested products modifies this induction of CD23; in fact, a decrease of less than 5% cannot be observed (n=8).

After the CD23 has been taken up by IgE-containing immune complexes, the production of a large number of mediators and cytokines (in particular TNF) and of products resulting from the oxidative metabolism, such as nitrogenous derivatives, is induced. This stimulation redefines in vitro an allergic-type inflammatory reaction.

TABLE 6A

Production of nitro derivatives ($NO_2^-$ in μM) after stimulation by IgE-containing immune complexes (IL-4) +/− 10 6mg/ml of the products K17 and K18

| Cells | | Expt-1 | Expt-2 | Expt-3 | Expt-4 |
|---|---|---|---|---|---|
| Macrophages | | 15(5)* | 18(3) | 25(11) | 27(3) |
| | +K17 | 16(3) | 17(6) | 19(7) | 30(6) |
| | +K18 | 7(2) | 6(4) | 10(2) | 7(2) |
| Keratinocytes | | 19(5)* | 22(1) | 13(1) | 7(1) |
| | +K17 | 16(3) | 20(3) | 14(2) | 7(6) |
| | +K18 | 4(2) | 7(4) | 9(2) | 3(2) |

*The values between brackets are those of cells which have not been stimulated by IgE-containing immune complexes.

The product K18 exhibits an inhibitory activity on the generation of nitro derivatives by the keratino-cytes and the macrophages stimulated by IL-4.

TABLE 6B

Production of TNF (pg/ml) after stimulation by IL-4 +/− K17 and K18

| Cells | | Expt-1 | Expt-2 | Expt-3 | Expt-4 |
|---|---|---|---|---|---|
| Macrophages | | 908(78)* | 135(40) | 508(45) | 712(58) |
| | +K17 | 917(45) | 102(41) | 510(41) | 700(32) |
| | +K18 | 524(59) | 98(35) | 420(32) | 333(25) |
| Keratinocytes | | 198(31)* | 105(10) | 128(10) | 132(15) |
| | +K17 | 185(35) | 111(31) | 120(32) | 132(40) |
| | +K18 | 95(23) | 60(35) | 25(12) | 35(12) |

*The values between brackets are those of cells which have not been stimulated by IgE-containing immune complexes, ND = non-detectable.

The product K18 exhibits an inhibitory activity on the generation of TNF by the macrophages and the kertinocytes stimulated by IL-4.

It therefore appears that K18 possesses a non-specific and allergic-type anti-inflammatory activity whereas the product K17 only has a non-specific anti-inflammatory activity.

Consequently, the effects of the product K18 were evaluated as a function of the dose. The results are illustrated in FIG. 1.

K18 therefore inhibits, in a dose-dependent way, the generation of nitro derivatives and also of TNF. The results thus obtained demonstrate that K18 exhibits a generally advantageous anti-inflammatory activity and that this activity is similar to that of H37.

EXAMPLE 2

Demonstration of an activity synergy between CM-β-glucan (K18) and ginkgo extract (H37)

The anti-inflammatory activities of K18 and H37 and of their combination respectively are determined.

The tests are carried out in a keratinocyte model, as indicated in Example 1 (Materials and Methods) after stimulation, on the one hand, by an IFN-γ+ LPS combination and, on the other hand, by IL-4 and IgE-containing immune complexes.

As shown in FIG. 2, the products K18 and H37 act in synergy in their anti-inflammatory functions.

It should be recalled that this anti-inflammatory activity covers the non-specific and allergic anti-inflammatory activity.

EXAMPLE 3

Analysis of the prevention of detrimental cutaneous changes obtained by UV A and UV B irradiation of human skin Organ cultures are produced according to the following protocol: 10 skin fragments from different donors (source:plastic surgery) are placed in inserts which are themselves positioned over culture wells. Culture medium (antibiotics, FCS) is added to the bottom of the wells, passage between the two compartments being achieved by slow diffusion via a porous membrane (0.45 μm).

Before each irradiation, each cosmetic cream (2 mg/cm$^2$) is deposited directly on the skin for 2 hours (control skins without treatment will be analysed in parallel). The 3 creams and the excipient are renewed three times per week on the skins:

cream 1: 0.5% CM-glucan
cream 2: 0.05% Ginkgo biloba
cream 3: CM-glucan+Ginkgo biloba extract (H37)
cream 4: excipient (Carbopol placebo)

After having removed the surplus cream, the skin is then irradiated with 12 J/cm² of UV A and 6 J/cm² of UV B (Vilber Lourmat T40 M lamp), equivalent to 20 DEM, doses determined by a preliminary study which make it possible to rapidly obtain lesions at the level of the epidermis and dermis with, in particular, detrimental changes in the collagen and elastic fibres. These doses are, moreover, equivalent to the doses used for the photopatch tests and to the doses used in hairless murine models for generating sunburn cells.

Irradiation is carried out every other day. Three exposure sessions are carried out and then the skin fragments are collected for the following analyses.

The production of oxygen derivatives, such as nitric oxide (NO), shows attack by UV radiation.

The possible protection contributed by the creams will be quantified by evaluating the decrease in the amount of nitrites and the increase in SOD.

1) Quantitative determination of nitric oxide and of nitrites

Nitric oxide, NO, is an important physiological mediator, not only as vasodilator and neurotransmitter but also as pro-inflammatory agent. Its synthesis is mediated by an enzyme, NO synthase, which is expressed by many cell types and in particular keratinocytes, when they are activated.

NO, obtained by oxidation of L-arginine by NO synthase, is an unstable product which is rapidly degraded to nitrites ($NO_2$) and nitrates ($NO^3$). It is the spectrophotometric quantitative determination of the nitrites in the culture supernatant in the presence of Griess's reagent which reveals the NO synthase activity.

The results are reported in the table below.

Quantitative determination of the nitrites

|  | (nmol/ml) | % of protection |
|---|---|---|
| Skin treated with cream 1 | 21.6 ± 7.3 | 14.7% ± 8.2 |
| Skin treated with cream 2 | 21.4 ± 3.6 | 13.5% ± 5.8 |
| Skin treated with cream 3 | 16.4 ± 2.9* | 33.8% ± 2.3* |
| Skin treated with cream 4 | 24.9 ± 5.3 |  |

*Statistically significant result ($p < 0.05$; Student's test)

The percentage of protection was calculated in the following way: (A−B/A)×100 where A is the result with cream No. 4 and B the result which cream 1, 2 or 3.

The skins treated with creams 1 and 2 exhibit a slight decrease (not significant) in the production of nitrites. The greatest decrease is obtained with skins treated with cream 3, a difference which is statistically significant with respect to the excipient. Calculation of the percentage of protection confirms these results, cream 3 having in particular a protection of 34%.

2) Quantitative determination of SOD

Attack by U.V. radiation is reflected by a decrease in the level of SOD.

The activity of superoxide dismutase is determined by the technique of McCord and Fridovich. Briefly, superoxide anions are generated by the action of xanthine oxidase on xanthine. The SOD present in the samples can then inhibit the reduction of cytochrome C by these superoxide anoins. The activity of the SOD is related to the amount of reduced cytochrome C remaining in the reaction medium.

The results are expressed by percentages of inhibition with respect to the excipient (cream No. 4): the SOD hydrolyses a portion of the free radicals generated by the U.V. attack and the xanthine/xanthine oxidase system. Thus, the decrease in the optical density (proportional to the amount of free radicals) will make it possible directly to quantify the level of SOD.

Quantitative determination of SOD

|  | % of inhibition |
|---|---|
| Skin treated with cream 1 | 11.1% ± 3.4 |
| Skin treated with cream 2 | 7.04% ± 2.9 |
| Skin treated with cream 3 | 15.1% ± 3.3* |

*Statistically significant result ($p < 0.05$: Student's test)

With respect to the excipient, the skins treated with creams 1 and 2 show a slight protection (not significant) against the decrease in the SOD activity induced by UV radiation. This protection is greater with the skins treated with cream 3, a difference which is statistically significant with respect to the excipient.

Conclusion

Quantitative determination of the nitrites has demonstrated, for skins treated with cream No. 3, a significant decrease in their amount with respect to the excipient. These results make it possible to envisage the protective activity of cream No. 3 with respect to the detrimental dermal changes generated by inflammatory components. Skins treated with creams 1 and 2 have only a tendency towards protection. There therefore exists a synergy between the components of cream No. 3.

Quantitative determination of SOD seems to confirm this analysis with protection of skins treated with cream No. 3 with respect to detrimental radical changes generated by U.V. radiation. Skins treated with creams 1 and 2 have only a tendency towards protection, more marked in the case of cream No. 1.

EXAMPLE 4

Compositions containing combinations according to the invention

|  | % |
|---|---|
| A) Formulation with depigmenting agents |  |
| Water | 70.965 |
| Octyl methoxycinnamate | 6.000 |
| Glyceryl stearate/PEG-100 stearate | 5.000 |
| Glycerol | 5.000 |
| $C_{12}$–$C_{15}$ alkyl benzoate | 4.000 |
| Petrolatum | 1.500 |
| Cetyl palmitate | 1.000 |
| Cetyl alcohol | 1.000 |
| Stearyl alcohol | 0.500 |
| Sodium sulphite | 0.025 |
| Sodium disulphite | 0.025 |
| Hydroquinone | 2.000 |
| Citric acid | 0.15 |
| Carbomer | 0.300 |
| Tocopheryl acetate | 0.100 |
| Phenoxyethanol | 0.730 |
| Methylparaben | 0.200 |
| Propylparaben | 0.070 |
| Sodium hydroxide | 0.135 |
| Disodium EDTA | 0.200 |
| β-Glucan | 1.0 |
| Ginkgo biloba extract | 0.1 |
| B) Formulation with retinol |  |
| Water | 56.42 |
| Cetearyl octanoate | 9.00 |
| Octyl methoxycinnamate | 8.00 |
| Lactose | 5.00 |

-continued

|  | % |
|---|---|
| Glycerol | 5.00 |
| Hydrogenated groundnut oil | 5.00 |
| Glyceryl polymethacrylate | 3.45 |
| Butylmethoxydibenzoylmethane | 1.50 |
| Isopropyl myristate | 1.00 |
| Hydrogenated lecithin | 1.00 |
| β-Glucan | 1.00 |
| Ammonium hydroxide | 0.75 |
| Phenoxyethanol | 0.73 |
| $C_{10}$–$C_{30}$ Alkyl acrylate copolymer/acrylates | 0.50 |
| Poloxamer 407 | 0.50 |
| Tocopheryl acetate | 0.50 |
| Methylparaben | 0.20 |
| Ginkgo biloba extract | 0.10 |
| Carbomer | 0.10 |
| BHT | 0.10 |
| Propylparaben | 0.07 |
| Propylene glycol | 0.05 |
| Retinol | 0.03 |
|  | 100.00 |

C) Formulation with retinol

|  |  |
|---|---|
| Water | 69.689 |
| Octyl hydroxystearate | 6.2942 |
| Glycerol | 4.0000 |
| Ceteareth-20/stearyl alcohol | 3.0000 |
| Ceteateth-20/cetearyl alcohol | 3.0000 |
| Glyceryl distearate | 2.8000 |
| Dimethicone | 2.5000 |
| $C_{12}$–$C_{15}$ Alkyl lactate | 1.5000 |
| Steareth-10 | 1.4000 |
| Cholesterol | 1.0000 |
| Acetylated lanolin alcohol/cetyl acetate | 1.0000 |
| Polysorbate 80 | 0.7000 |
| Sodium citrate | 0.5160 |
| $C_{13}$–$C_{14}$ Isoparaffin/laureth-7 | 0.5000 |
| Stearyl alcohol | 0.5000 |
| Polysorbate 20/retinol | 0.1058 |
| BHT | 0.1000 |
| Methylparaben | 0.2000 |
| Fragrance | 0.0500 |
| Propylparaben | 0.0300 |
| Citric acid | 0.0150 |
| Ginkgo biloba extract | 0.1 |
| Panthenol | 1.0 |
|  | 100. |

D) Formulation with tretinoin

|  |  |
|---|---|
| Tretinoin | 0.05 g |
| β-Glucan | 0.50 g |
| Ginkgo biloba extract | 0.10 g |
| Light liquid paraffin | 25.00 g |
| Non-crystallizable 70 percent sorbitol solution | 5.00 g |
| Hydroxyoctacosanyl hydroxystearate | 5.00 g |
| Methoxymacrogol 22/dodecyl glycol copolymer | 5.00 g |
| Macrogol 45/dodecyl glycol copolymer | 3.00 g |
| Stearoxytrimethylsilane and stearyl alcohol | 1.00 g |
| Dimethcone | 1.00 g |
| Fragrance | 0.25 g |
| Methyl para-hydroxybenzoate | 0.20 g |
| Sodium edetate | 0.10 g |
| Quaternium 15 | 0.10 g |
| Butylated hydroxytoluene | 0.10 g |
| Citric acid monohydrate | 0.10 g |
| Purified water | 53.495 g |

What is claimed is:

1. A method for treating sensitive or allergic skin by topically applying to said skin a composition comprising at least two compounds chosen from components having at least two activities selected from the group consisting of: a) anti-radical, b) anti-inflammatory and c) anti-allergic activity, wherein said composition comprises compounds having anti-radical, anti-inflammatory and anti-allergic activity.

2. A method according to claim 1 wherein said compounds exhibiting an anti-radical activity are chosen from the group consisting of free-radical scavengers, anti-lipoperoxidants and stimulants of the endogenous production of the enzymes which degrade free radicals or a combination thereof.

3. A method according to claim 1 wherein said compounds exhibiting an anti-inflammatory activity are chosen from the group consisting of prostaglandin inhibitors, inhibitors of cytokine production and inhibitors of leukotriene production or a combination thereof.

4. A method according to claim 1 wherein said compounds exhibiting anti-allergic activity are chosen from the group consisting of inhibitors of lymphocyte proliferation, inhibitors of the internalization of HLA receptors and inhibitors of cytokine production or a combination thereof.

5. A method according to claim 1 comprising the topical application of said composition to the skin to inhibit the synthesis or the expression of neuromediators by cutaneous cells.

6. A method according to claim 1 wherein at least one compound is chosen from the following group: Ginkgo biloba and its extracts, iramine, D-panthenol, β-sitosterol, modulene, α-tocopherol and its derivatives, α-tocopherol phosphate, β-glucan and its derivatives, eicosapentanoic acid, 18 β-glycyrrhetinic acid, glycyrrhetinic acid monoglucoronide, stearyl glycyrrhetinate, Scutellaria extract, lactoferrin, green tea extract, vitamin C glutathione, epidermal thymus factor, imidazole derivatives, triazole derivatives and lipacid, provided that said composition excludes the combination of vitamin E and Scutellaria extract.

7. A method according to claim 6, wherein at least two components are chosen from the following group: Ginkgo biloba and its extracts, iramine, D-panthenol, β-sitosterol, modulene, α-tocopherol and its derivatives, α-tocopherol phosphate, β-glucan and its derivatives, eicosapentanoic acid, 18 β-glycyrrhetinic acid, glycyrrhetinic acid monoglucoronide, stearyl glycyrrhetinate, Scutellaria extract, lactoferrin, green tea extract, vitamin C glutathione, epidermal thymusfactor, imidazole derivatives, triazole derivatives and lipacid, provided that said composition excludes the combination of vitamin E and Scutellaria extract.

8. A method according to claim 7 comprising the topical application of a composition comprising at least one of the combinations selected from the group consisting of: α-tocopherol/Ginkgo biloba extract, carboxymethyl-β-glucan/Ginkgo biloba extract, β-sitosterol/D-panthenol, drieline/lactoferrin and panthenol/green tea extract.

9. A composition with hypoallergenic or immunomodulatory activity or which is intended for the treatment of sensitive skin made in accordance with the process comprising the steps of:

a) selecting compounds which exhibit a least one anti-inflammatory, anti-radical and/or anti-allergic activity, at least two of such compounds exhibiting at least two different activities;

b) combining said compounds and determining whether at least one of the activities is potentiated by the combination of said compounds;

c) selecting at least one of the combinations of compounds in which said activities is potentiated; and d) mixing at least one of the selected combinations with dermatologically or cosmetologically acceptable excipients, in order to obtain a composition having hypoallergenic or immunomodulatory activity provided that said composition excludes the combination of vitamin E and Scutellaria extract;

wherein said composition comprises at least on component chosen from the group consisting of Ginkgo biloba and its extracts, iramine, D-panthenol, β-sitosterol, modulene, α-tocopherol and its derivatives, α-tocopherol phosphate, β-glucan and its derivatives, eicosapentanoic acid, 18 β-glycerrhetinic acid, glycyrrhetinic acid monoglucoronide, stearyl glycyrrhetinate, Scutellaria extract, lactoferrin, green tea extract, vitamin C glutathione, epidermal thymusfactor, imidazole derivatives, triazole derivatives and lipacid, provided that said composition excludes the combination of vitamin E and Scutellaria extract, wherein said composition comprises a concentration of Ginkgo biloba extract containing a terpene concentration which is less than 1% w/w of dry matter in an amount of from about 0.001% to about 10% w/w and β-glucan which is substituted by carboxymethyl groups.

* * * * *

UNITED STATES PATENT AND TRADEMARK OFFICE
CERTIFICATE OF CORRECTION

PATENT NO.    : 6,352,698 B1
DATED         : March 5, 2002
INVENTOR(S)   : Castelli et al.

It is certified that error appears in the above-identified patent and that said Letters Patent is hereby corrected as shown below:

Column 1,
Line 6, insert after Title:
-- CROSS REFERENCE TO RELATED APPLICATIONS:
This application is the national filing of International Application PCT/IB97/01218 Filed on October 21, 1997. --

Signed and Sealed this

Second Day of August, 2005

JON W. DUDAS
*Director of the United States Patent and Trademark Office*